United States Patent [19]

Beurskens

[11] Patent Number: 4,682,220
[45] Date of Patent: Jul. 21, 1987

[54] APPARATUS FOR DETECTING CONTAINERS HAVING A DEVIATING PROPERTY

[75] Inventor: Godefridus P. F. Beurskens, Bathmen, Netherlands

[73] Assignee: Hajime Industries Ltd., Tokyo, Japan

[21] Appl. No.: 730,039

[22] Filed: May 3, 1985

[30] Foreign Application Priority Data

May 3, 1984 [NL] Netherlands ................ 8401416

[51] Int. Cl.⁴ ............................................. H04N 7/18
[52] U.S. Cl. ............................... 358/106; 250/223 B
[58] Field of Search .................... 358/106, 101, 107; 382/1, 18; 250/223 B; 356/240; 209/522

[56] References Cited

U.S. PATENT DOCUMENTS

| | | | |
|---|---|---|---|
| 4,026,414 | 5/1977 | Ellinger | 250/223 B X |
| 4,293,214 | 10/1981 | Ducloux | 250/223 B X |
| 4,391,373 | 7/1983 | Wiggins | 250/223 B X |
| 4,454,542 | 6/1984 | Miyazawa | 250/223 B X |
| 4,491,728 | 1/1985 | Fischer | 250/223 B |
| 4,498,003 | 2/1985 | Cibis | 250/223 B |
| 4,508,453 | 4/1985 | Hara et al. | 358/106 X |
| 4,528,810 | 3/1986 | MacFarlane et al. | 358/106 X |
| 4,532,650 | 7/1985 | Wihl et al. | 358/106 X |
| 4,546,247 | 10/1985 | Peyton et al. | 250/223 B |

FOREIGN PATENT DOCUMENTS 2916361 11/1980 Fed. Rep. of Germany ...... 358/101

Primary Examiner—James J. Groody
Assistant Examiner—Victor R. Kastah
Attorney, Agent, or Firm—John P. Snyder

[57] ABSTRACT

To inspect objects which are symmetrical, as for example the rims of bottles, the video signal representing a field of view within which the rim is imaged is divided into portions which should contain mirror image portions of the rim image. These two image portions are compared electronically to determine the deviation, if any, from such mirror image symmetry. If the deviation is sufficiently great, the object being inspected is earmarked for rejection. The division into image portions is by the top and bottom of a strip of the composite image in which the strip is perpendicular to the raster lines of the field of view and by left- and right-hand portions of the composite image on either side of the strip. The electronic comparison is effected by counting the scanning points along a raster line, line by line, containing the image of the rim and comparing the counts obtained from the two image portions to each other. The image of the rim should be centered within the field of view.

4 Claims, 16 Drawing Figures

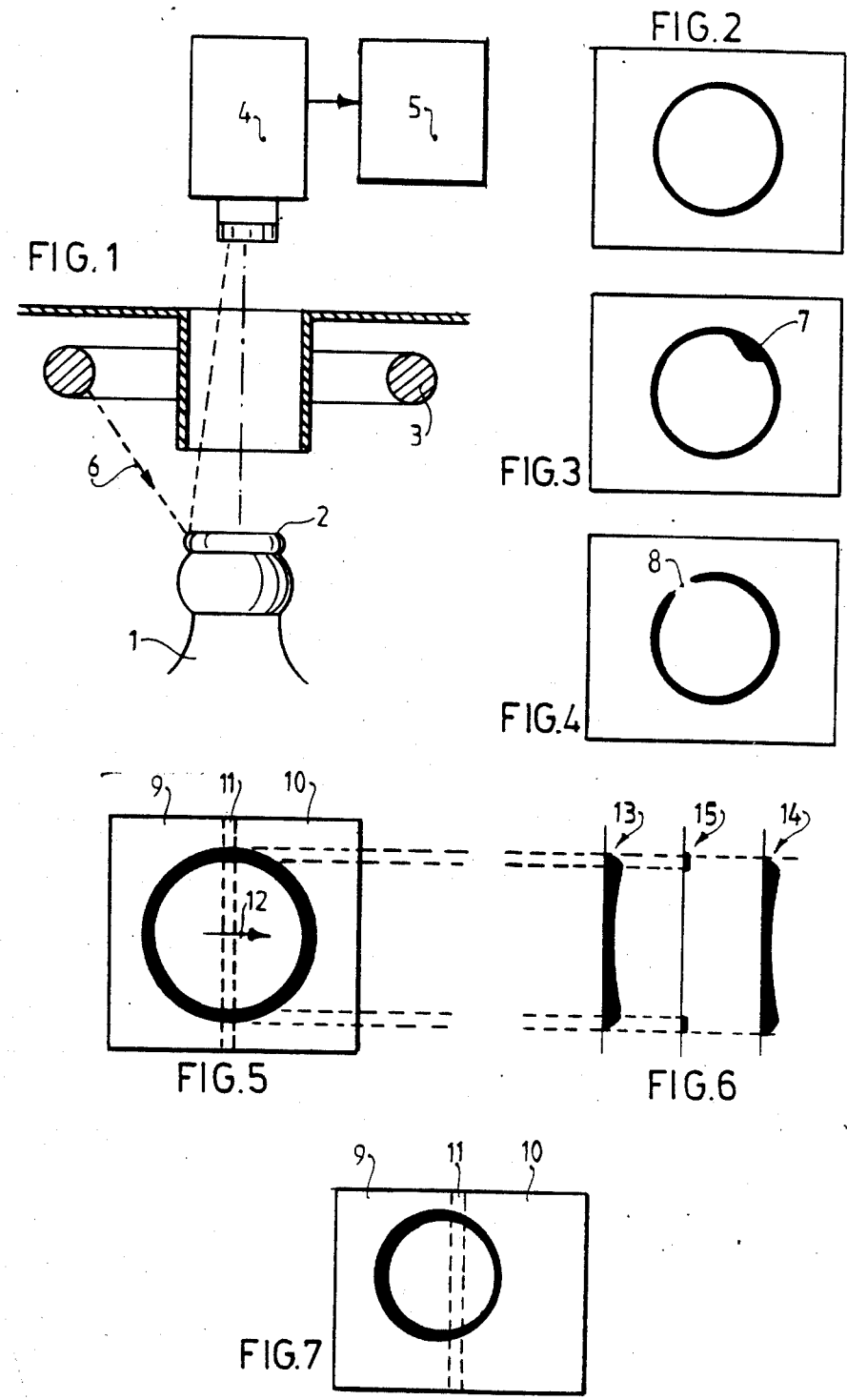

APPARATUS FOR DETECTING CONTAINERS HAVING A DEVIATING PROPERTY

BACKGROUND

The invention relates to an apparatus for detecting containers having at least one property deviating from a previously set standard, said containers comprising a convex, circular symmetrical reflecting upper rim, said apparatus comprising: an illumination station and a video camera for forming a video signal corresponding with the video picture of the upper rim of a container to be checked, a video signal processing unit for comparing the video picture with the picture corresponding with the standard previously set, and generating in dependency of the result of said comparison an approval or rejection signal, respectively.

The illumination station may be in the form of annular illumination station for illuminating the upper rim of respective containers conveyed by a transport apparatus, said illumination station illuminating the upper rim due to which the video camera is able to form the picture of the reflection ring of the upper rim. As an alternative use can be made of a technique, in which the broadened upper rim extends a little over a diffusely reflecting surface, e.g. by transporting the containers by two co-operating starwheels, in which the video camera forms a picture of the upper rim and this upper rim remaining non-illuminated. If necessary also use can be made of light transmitted through the bottom, due to which the upper rim forms a shadow against a lighter background. The description following hereafter will, as an explanation of the invention, only relate to the first-mentioned technique, according to which the upper rim reflects light.

The standard in question can be e.g. the smoothness, evenness, annular shape, or the like of the upper rim, which can be important in view of e.g. closing the container, particularly a glass bottle by means of e.g. a crown cap. Further rough surfaces, cracks, broader portions and the like are properties which may be laid down in a standard, deviations of which may give raise to problems during the processing of the containers.

A deviation of a somewhat different category is the possible crookedness of in particular glass bottles. Crookedness in this case can be interpreted as a deviation in the co-axial positioning of the bottom and the plane of the upper rim. As a result of such a deviation, which particularly may exists in glass bottles, as the production thereof is not always in practice a procedure controllable in every respect, when a bottle is positioned under a filling nozzle a deviation of the desired position of the neck with respect to the position of the mouth opening of the filling tube may be caused, due to which the bottle is not filled or insufficiently filled, the filling apparatus can be polluted and in closing the bottle there is a chance that the related cap or cork cannot be placed in the correct manner.

From the European patent application No. 0 046 241 an inspection apparatus is known, in which an analogue video signal is used. A progressing average of subsequent video lines is used as a reference, after which an individual video line is compared with said reference.

Furthermore a European patent application No. 0 101 246 exists, in which a technique is described for assessing the crookedness of glass containers. Experience has taught that with the way of illuminating shown therein, namely through the walls in the direction of the bottom, in particular with dark coloured bottles there is so little light reflected from the bottom into the direction of the video camera positioned above the bottles, that the apparatus is unreliable in practice and for large classes of bottles even not fit for use.

Furthermore reference is made to the German patent application No. 29 16 361 laid open for public inspection, an addition to German patent application No. 28 48 316.

All publications mentioned describe the basic configuration of the apparatus mentioned in the preamble.

SUMMARY OF THE INVENTION

The invention has for its purpose to engineer such an apparatus in such a way that it operates very reliably, can be used for substantially all classes of containers and is adapted to assess the properties of the upper rim of the containers and furthermore the degree of crookedness of these containers, and to engineer an inspection-apparatus in such a way, that existing apparatus can be rebuilt by means of relatively simple means and therefore economically into an apparatus according to the invention.

In connection with the above the invention provides an apparatus of the type set forth above, which is characterized in that said video signal processing unit is adapted for separating the video picture in two mirror symmetrical parts with respect to a line extending perpendicularly to the picture lines, further characterized in that means are present for counting the number of representative picture information elements per picture line in each of said both parts and for mutually comparing them, and in that means are present for comparing the result of said comparison with the video picture corresponding with the standard previously set and generating in dependency of the result of said comparison, an approval or rejection signal, respectively.

If the reflecting upper rim of a container is illuminated by means of an annular illumination station, the station gives, in dependency of the distance between that upper rim and the illumination station an annular reflection ring on said rim.

During a test with damaged bottles it has appeared that a changing of said reflection ring occurs at the majority of the errors found. If the fracture plane of an error exhibits such an angle relative to the illumination and the video camera that also reflection occurs, the ring exhibits a broader portion at the location of the error. If the fracture plane exhibits such an angle, that no reflection occurs in the direction of the camera, then the nominally circular-shaped reflection ring is interrupted.

In certain cases use can be made of a variant, in which the video signal processing unit forms, in the region of the separation between the two parts, also an intermediate zone and the counting means also assess the number of representative picture information elements per picture line in said intermediate zone for forming a reference. In the intermediate zone, from the number of video lines in which picture information elements are counted and the place thereof, the thickness of the reflection ring can be deduced, together with the occurrence of a reflecting inner ring and the position of the reflection ring in the video picture. With this information as a reference the information in the two picture parts, which for obvious reasons will be indicated as histogram-regions may be interpreted to detect interruptions and/or broader portions.

The next following assessments can be made, e.g. in parallel, by using microprocessors:
(1) comparing both regions;
(2) the assessment of the magnitude of an interruption by counting the number of video lines in which no picture information elements are present;
(3) the assessment of a broader portion by comparing the number of picture information elements in a video line with that number in other line or a reference line (e.g. an average of a number of lines);
(4) the assessment of interruptions or broader portions in the intermediate zone. Interruptions can be assessed by determining the number of lacking picture information elements of the line or lines having the largest number of picture information elements for the upper and lower parts relative to the chosen thickness of the intermediate zone. A comparison may be made between the upper and the lower parts; particularly the difference in the number of picture information elements may be determined. Broader portions can be assessed by determining the width, i.e. in a direction perpendicular to the video lines, in other words: assessment of the number of video lines, in the intermediate zone, in the upper part or the lower part. If a deviation from the standard appears in terms of a larger number of lines present, this indicates the presence of a broader portion. Also a comparison may be made between the upper and the lower parts.

A further possibility is the assessment of the width of the reflecting ring. This assessment can take place by the formation of a histogram, namely the number of video lines, graphically plotted against the number of picture information elements per line. In general, for containers within the tolerance region of the preselected standard here there will be a more or less symmetrical distribution. In case of the presence of a dramatically broader portion, a plug or a crown cap, a more or less substantial shifting to the right may occur, which means a shifting of the total histogram distribution in the direction of a larger number of picture information elements per line. For the left picture part and the right picture part this assessment may take place separately.

From the said histogram also a start-reference can be deduced for the determination of small broader parts in the left and the right picture parts. In subsequent determination the reference may be floating, if wanted.

After comparison of the above results with a standard to be choosen a bottle may be accepted or rejected.

The picture information elements can be pixels or contrast transients.

An embodiment which is adapted for the above-mentioned crookedness of a container can be characterized in that the illumination station generates a flash any time when a container passes with the axis of its bottom the axis of the illumination station and the optical axis of the video camera.

An embodiment which is adapted for checking the upper rim of a container can be characterized in that the illumination station generates a flash any time when a container passes with the axis of upper rim the axis of the illumination station and the optical axis of the video camera.

In connection with the mentioned determination of the crookedness of a container it should be noted that the reflection ring with a crooked container will not appear in the middle of the video picture, but somewhere else, whilst furthermore the shape of the reflection ring can deviate from the annular shape and exhibit a varying width.

THE DRAWINGS

The invention will now be explained with reference to the drawing. In the drawing show:

FIG. 1 a strongly schematized picture of an apparatus according to the invention;

FIG. 2 the video picture of a good bottle;

FIG. 3 the video picture of a bottle, in which the error in the upper rim causes an additional reflection;

FIG. 4 the video picture of a wrong bottle, in which the error causes an interruption in the reflection ring;

FIG. 5 a video picture of a bottle, subdivided into three regions;

FIG. 6 the histograms of the picture information elements, corresponding with the picture according to FIG. 5;

FIG. 7 the video picture of a crooked bottle; and

FIGS. 8, 9-16 a graph and schematized video pictures, respectively, for illustrating the possibilities to evaluate the video picture according to the invention.

DETAILED DESCRIPTION

FIG. 1 shows a bottle 1 having a reflecting upper rim 2, which is illuminated by an annular flash bulb 3. The reflection pattern of the upper rim is sensed by a video camera 4 that supplies its output signals to a video signal processing unit 5. Reference number 6 refers schematically to the path of the rays.

For a good bottle, i.e. a bottle of which has no property to be tested which deviates from a standard previously set, the video camera provides a video picture as shown in FIG. 2. This video picture exhibits an annular pattern with the same thickness along its whole circumference and a substantially pure circular shape.

FIG. 3 shows a broader part 7 which is indicative of the fact that the upper rim of the bottle exhibits a deviation, e.g. a fracture surface with causes an additional reflection.

FIG. 4 shows an interruption 8 in the annular shape which is indicative of the fact that a deviation is present which causes no reflection into the direction of the video camera.

Figure 8:
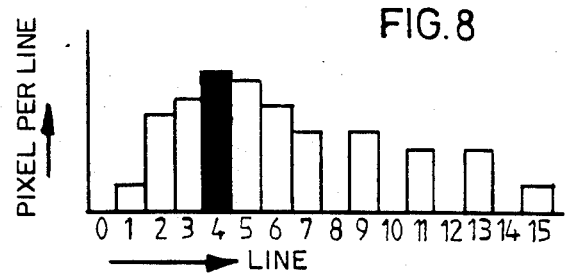

FIG. 5 shows the subdivision of the video picture in a left hand part 9, a right hand part 10 and a narrow intermediate zone 11. The video scanning takes place in the direction indicated with arrow 12. The video signal processing unit 5 forms the subdivision shown in FIG. 5 of the video picture and forms on basis of this picture the three digitalized patterns according to FIG. 6 which are stored as tables. The left hand pattern 13 corresponds with the number of picture information elements per line or per equal number of lines of the picture part 9, the right hand pattern 14 corresponds with the picture part 10, whilst the middle pattern 15 shows the same data for the narrow intermediate zone 11.

It will be obvious that the width of the two separated parts of pattern 15 corresponds with the width of the reflection ring shown in FIG. 5.

For the ideal case according to FIGS. 5 and 6 patterns 13 and 14 are identical. For the case according to FIG. 3 the right hand pattern 14 will cause a larger value in a certain zone, whilst in the case according to FIG. 4 the left hand pattern exhibits in a certain zone a lowered value. On basis of a criterium to be choosen a bottle according to FIGS. 3 or 4 can, if necessary, be rejected and expelled.

The intermediate zone 11 has a plurality of functions. It may serve for the determination of the position of the rim. Further the number of video lines over which the pattern according to FIG. 6 extends is indicative for the width of the reflection ring. By means of the pattern 15 it can also be determined, whether there is possibly an upper rim of a bottle having a shape which is deviating from a generally half-toroidal shape, e.g. the presence of more than one rim. Also by studying the pattern 15 furthermore a tolerance measure can be determined for judging patterns 13 and 14 in view of interruptions, broader portions and/or damaged portions.

FIG. 7 at last shows a video picture of a crooked bottle. It will be clear that it has an excentric positioning, whilst the reflection ring also exhibits a varying thickness.

FIGS. 8-16 relate, by way of example, the inspection of the upper rim of containers, without determination of the crookedness as has been discussed above. In the technique to be described hereinafter the point is to accept or reject an inspected container. Thereto several criteria may be used. In general a number of subsequent criteria will be used, as discussed hereinafter. As soon as, on basis one of the criteria, it is determined that the upper rim is damaged further inspection will not take place and the related container is expelled.

FIG. 8 shows a graph of the number of video lines as a function of the number of picture information elements, particularly pixels. The black bar (4 pixels) indicates that the variation of the thickness of the ring can be determined by looking for the number of white pixels per line, which is appearing the most frequently.

Figure 9:
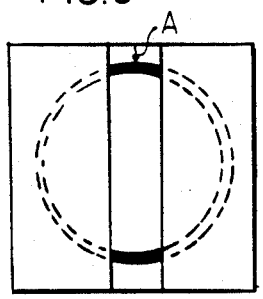

FIG. 9 shows the calculation of the position of the top of the ring in the intermediate zone. Thereto the first line having white pixels is searched, starting with the upper side of the picture.

Figure 10:
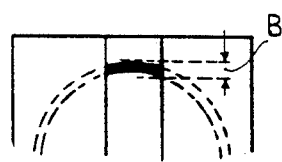

FIG. 10 shows the calculation of the thickness of the ring in the intermediate zone, by counting the number of lines having white pixels.

Figure 11:
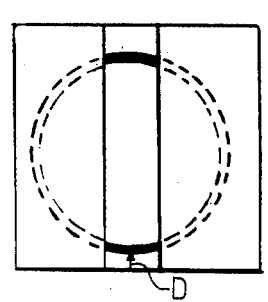

FIG. 11 shows the calculation of the lower side of the ring analogous to the determination according to FIG. 9.

Figure 12:
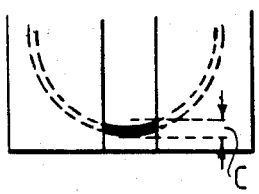

FIG. 12 shows the calculation of the thickness of the lower part in the intermediate zone, fully analogous to the determination according to FIG. 10. Subsequently the difference between the number of white pixels can be determined between the upper and the lower parts of the intermediate zone.

Figure 13:
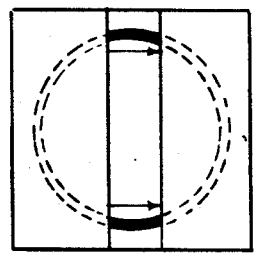

FIG. 13 shows a possible determination of interruptions in the intermediate zone. Hereto the line having the largest number of white pixels is searched. If one knows the maximum number of white pixels, the interruptions can be calculated.

Figure 14:
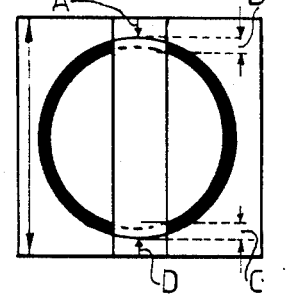

FIG. 14 shows, how the diameter of the ring might be calculated in terms of the number of picture lines. Use is made of previous determinations according to FIGS. 9-12.

Figure 15:
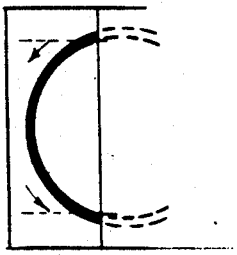
Figure 16:
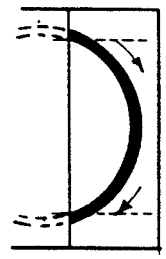

FIGS. 15 and 16 show a possible determination of interruptions and broader portions in the left hand and the right hand picture parts. Interruptions are assessed by determining in the case of value zero in the one picture part the number of white pixels in the other picture part. Broader portions will cause a larger number of white pixels per line. The number of pixels in this broader part is counted.

The criteria used can be expressed in terms of six tolerances:

tolerance 1 relates to interruptions in the left hand and right hand picture parts;

tolerance 2 relates to broader portions in the left hand and the right hand picture parts;

tolerance 3 relates to the difference between the upper and the lower parts in the intermediate zone;

tolerance 4 relates to interruptions therein;

tolerance 5 relates to the thickness of the ring in the left hand and the right hand picture parts; the criterium here is absolute;

tolerance 6 is also an absolute one and relates to the thickness of the ring in the intermediate zone, therefore in the lower as well in the upper part thereof.

I claim:

1. The method of inspecting entities such as bottles each having a part thereof, such as the rim of a bottle, which is of symmetrical shape, which comprises the steps of:

moving entities along a predetermined path;

electronically imaging the part of each entity having a symmetrical shape to produce an electronic image thereof;

electronically comparing portions of each electronic image which should be mirror images of each other by scanning the entity with a raster of lines each having discrete imaging points thereon to determine the extent, if any, in deviation from mirror image symmetry therebetween, the step of electronically comparing being effected with respect to two portions of the image which are the top and bottom of a strip of the electronic image of each part extending centrally of the image and oriented perpendicular to the lines and also with respect to the two portions of the image which are respectively to the left and to the right of the strip; and accepting or rejecting the entity based upon the extent of deviation from mirror image symmetry determined during the step of electronically comparing the portions of the image which should be mirror images of each other.

2. The method as defined in claim 1 including the step of generating a rejection signal when the strip of electronically comparing indicates deviation of mirror image symmetry between the two portions of the image by a predetermined amount.

3. The method of inspecting entities such as bottles each having a part thereof, such as the rim of a bottle, which is of symmetrical shape, which comprises the steps of:

moving a sequence of entities along a predetermined path;

electronically scanning a field of view over a raster of lines each having scanning points thereon when the part of each entity having a symmetrical shape should be generally centered within the field of view, to produce an electronic image of each part;

electronically comparing two pairs of electronic image portions wherein each pair should be mirror images of each other to determine the extent, if any, in deviation from mirror image symmetry therebetween; and accepting or rejecting the entity based upon the extent of deviation from mirrror image symmetry determined during the step of electronically comparing, one pair of electronic image portions being the top and bottom portions of a relatively narrow strip of the electronic image of each part extending centrally of the field of view and oriented perpendicular to the lines and the other pair being the left- and right-hand portions of the field of view on either side of such strip.

4. The method as defined in claim 3 wherein the step of electronically comparing comprises counting the number of scanning points representing the image of the part per line in each pair of electronic image portions and mutually comparing such counts.

* * * * *

UNITED STATES PATENT AND TRADEMARK OFFICE
CERTIFICATE OF CORRECTION

PATENT NO. : 4,682,220
DATED : July 21, 1987
INVENTOR(S) : Godefridus P.F. Beurskens It is certified that error appears in the above-identified patent and that said Letters Patent is hereby corrected as shown below:

On the title page assignee should read

--(73) Assignees: Thomassen and Drijver-Verblifa N.V., The Netherlands and Hajime Industries Ltd., Tokyo, Japan, part interest --

Signed and Sealed this

Twenty-second Day of December, 1987

*Attest:*

DONALD J. QUIGG

*Attesting Officer*

*Commissioner of Patents and Trademarks*